July 31, 1973 M. TANTAU Plant Pat. 3,382
ROSE PLANT
Filed Nov. 17, 1971
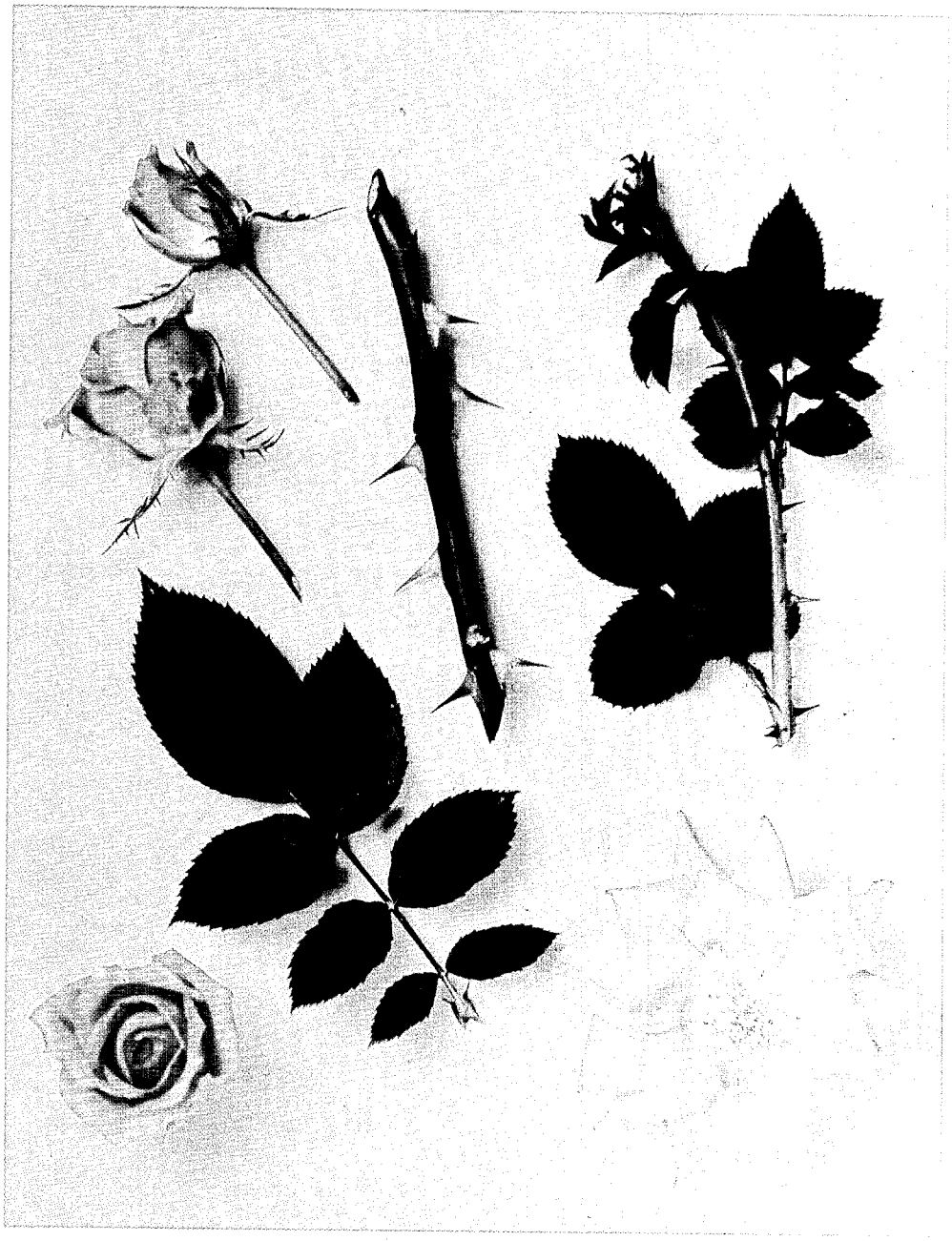
MATHIAS TANTAU
INVENTOR
BUCKHORN, BLORE, KLARQUIST & SPARKMAN
ATTORNEYS

United States Patent Office

Plant Pat. 3,382
Patented July 31, 1973

3,382

ROSE PLANT

Mathias Tantau, Schliebfach, Germany, assignor to Jackson & Perkins Company, Medford, Oreg.

Filed Nov. 17, 1971, Ser. No. 199,506
Int. Cl. A01h *5/00*
U.S. Cl. Plt.—25 1 Claim

This invention relates to a new and distinct variety of rose plant of the floribunda class originated bv crossing an unnamed seedling with Zorina, U.S. Plant Pat. 2,321.

The primary object of this breeding was to produce a new and improved rose variety of the floribunda class bearing flowers on a vigorous plant with better than usual foliage for cutflower purpose in the greenhouse to produce cutflowers of a marketable length in a new color.

This objective was fully achieved along with other desirable improvements as evidenced by the following unique combination of characteristics which are oustanding in the new variety and which distinguish it from its parents as well as from all other varieties of which I am aware:

(1) A medium sized flower (Zorina type), long lasting as a cutflower in a bronze-gold/orange color without paling and with a good fragrance.

(2) Abundant production of medium long cutflowers repeating very rapidly.

(3) For cutflower purpose side-buds have to be removed.

(4) It may be forced very early and it produces very firm stems.

(5) The color is very bright and very intense.

(6) Cutflowers may be stored in a cool environment for several days without losing any of their color intensity.

Asexual reproduction of my new variety by budding, as performed at 2082 Uetersen, Germany, shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new rose variety, with color terminology in accordance with Farbenordnung Hickethier, Osterwald, Hanover, Germany, except where general color terms of ordinary dictionary significance are obvious:

*Seedling*

Parentage:
- *Seed parent.*—Unnamed seedling.
- *Pollen parent.*—Zorina.

Classification:
- *Botanic.*—Rosa hybrid.
- *Commercial.*—Floribunda.

*Flower*

(Observations were made in August in Uetersen, Germany, of flowers grown in the greenhouse.)

Blooming habit: Recurrent—continuous.

Bud:
- *Size.*—⅓" when petals start to unfurl.
- *Form.*—Pointed.
- *Color.*—When sepals first divide—reddish-orange colored (Hickethier 960). When half blown—inside of petals—light orange color (Hickethier 940); reverse of petals—golden-orange colored, at the base more yellow (Hickethier 940).

- *Sepals.*—Color: Outside: Light greyish green with feltlike covering. Inside: Middle green, basis lighter green. Three appendaged sepals normally.
- *Receptacle.*—Color: Light green (603 Hickethier). Shape: Funnel. Size: Small. Surface: Smooth.
- *Peduncle.*—Length: Medium. Surface: Smooth. Color: Light green. Strength: Erect.

Bloom:
- *Size.*—Medium—average size when fully expanded (3").
- *Borne.*—Several together in pyramidal clusters.
- *Stems.*—Medium, normal.
- *Form.*—When first open—high centered. Permanence—retails its form to the end; outer petals curl back.
- *Petalage.*—Number of petals under normal conditions 32–35.
- *Color.*—Center of flower: Upper side of petals—copper-orange (950–940 Hickethier). Reverse of petals—golden-orange (950–920 Hickethier). Outer petals: Upper side of petals orange (940 Hickethier). Reverse of petals: Golden-orange (940–920 Hickethier). Base of petals: Yellow (820 Hickethier). General tonality from a distance—orange colored. The color changes a little. In spring and autumn it is more orange till reddish and in summer a little more yellow.
- *Discoloration.*—General tonality at end of first day—the same color; a little more yellow.
- *Fragrance.*—Moderate.

Petals:
- *Texture.*—Soft.
- *Surface.*—Inside—satiny. Reverse—satiny.
- *Shape.*—Oval.
- *Form.*—Tips slightly recurved; edges slightly quilled.
- *Arrangement.*—Informal, imbricated.
- *Petaloids in center.*—Few—small.
- *Persistence.*—Drop off cleanly.
- *Lastingness.*—On the plant—long. As cut flower—long.

Reproductive parts:
- *Stamens, anthers.*—Medium, many. Color—reddish brown; arrangement regular around styles.
- *Stamens, filaments (threads).*—Long. Color—yellow.
- *Pollen.*—Color—gold yellow.
- *Styles.*—Columnar, uneven lengths.
- *Stigmas.*—Color—red.
- *Ovaries.*—All enclosed in calyx.

*Fruit*

Form: Round headed.
Surface: Smooth.
Color at maturity: Scarlet red.
Sepals: Permanent, recurved.

*Plant*

Form: Bush.
Growth: Vigorous.
Foliage: Compound of 5 leaflets.
- *Size.*—Medium.
- *Quantity.*—Normal.
- *Color.*—New foliage: Reddish green. Old foliage: Dark green.

Leaflets:
- *Shape.*—Oval pointed.
- *Texture.* — Upper side — leathery. Underside—smooth. Ribs and veins—ordinary.
- *Edge.*—Serrated.
- *Serration.*—Single, sharp.
- *Petiole.*—Rachis—Color; green. Underside—prickles.
- *Stipules.*—Medium, serrated.

*Disease resistance.*—Resistant to mildew under normal growing conditions at Uetersen, Germany.

Wood:

*New wood.*—Color—reddish. Bark—smooth.

*Old wood.*—Color—green. Bark—smooth.

Thorns:

*Quantity.*—On main stalks from base—ordinary. On laterals from stalk—few.

*Form.*—Narrow based, long, straight.

*Color when young.*—Green and red.

*Position.*—Irregular.

*Pickles.*—Quantity: On main stalks—few. On laterals—none. Color: Brown.

*Short needles.*—Quantity: On main stalks—On laterals—none.

Other traits: These specifications were made of plants in the greenhouse. Habit of growth is similar to the greenhouse variety of Zorina and Minigold, being, however, nearer to Minigold.

I claim:

1. A new and distinct variety of rose plant of the floribunda class, substantially as herein shown and described, characterized particularly as to novelty by the unique combination of a vigorous, bushy, fast repeating habit of growth, leathery foliage, medium size, double flowers of a bronze-gold/orange color, outstanding as a medium sized cutflower.

No references cited.

ROBERT E. BAGWILL, Primary Examiner

PO-1050
(5/69)

UNITED STATES PATENT OFFICE
CERTIFICATE OF CORRECTION

Patent No. PP 3,382 Dated July 31, 1973

Inventor(s) Mathias Tantau

It is certified that error appears in the above-identified patent and that said Letters Patent are hereby corrected as shown below:

Column 2, line 14, "retails" should read --retains--.
Column 3, line 13, after "stalks-" insert --few--.

Signed and sealed this 27th day of November 1973.

(SEAL)
Attest:

EDWARD M.FLETCHER,JR.
Attesting Officer

RENE D.TEGTMEYER
Acting Commissioner of Patents